United States Patent
Smith et al.

(10) Patent No.: US 8,198,220 B2
(45) Date of Patent: Jun. 12, 2012

(54) WELLBORE TREATMENT COMPOSITIONS COMPRISING HYDROPHILICALLY MODIFIED POLYMERS AND NONIONIC SURFACTANTS

(75) Inventors: Philip S. Smith, Houston, TX (US); Dale L. Handlin, Jr., Shelby, NC (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 13/288,705

(22) Filed: Nov. 3, 2011

(65) Prior Publication Data

US 2012/0111570 A1  May 10, 2012

Related U.S. Application Data

(62) Division of application No. 12/565,621, filed on Sep. 23, 2009, now Pat. No. 8,076,270.

(60) Provisional application No. 61/100,467, filed on Sep. 26, 2008.

(51) Int. Cl.
  *C09K 8/68* (2006.01)
  *C09K 8/60* (2006.01)
  *E21B 43/16* (2006.01)

(52) U.S. Cl. ........... 507/203; 166/305.1; 507/209; 507/211; 507/213; 507/214; 507/217; 507/219; 507/224; 507/225; 507/904

(58) Field of Classification Search ........... 507/203, 507/209, 211, 213, 214, 217, 219, 224, 225, 507/904; 166/305.1
See application file for complete search history.

(56) References Cited

U.S. PATENT DOCUMENTS

| | | | | |
|---|---|---|---|---|
| 4,435,217 | A * | 3/1984 | House | 106/181.1 |
| 4,520,178 | A * | 5/1985 | Sakata et al. | 526/200 |
| 4,561,985 | A * | 12/1985 | Glass, Jr. | 507/108 |
| 2007/0281869 | A1 * | 12/2007 | Drochon et al. | 507/219 |
| 2009/0209438 | A1 * | 8/2009 | Thieme et al. | 507/219 |

* cited by examiner

*Primary Examiner* — Timothy J. Kugel
(74) *Attorney, Agent, or Firm* — Albert K. Shung (57) ABSTRACT

The disclosed compositions and methods utilize hydrophilic polymers modified by the incorporation of one or more hydrophilic side groups. The polymers may exhibit physical association in solution at a specific temperature so as to provide a significant increase in viscosity at the specific temperature. The viscosity of such systems is substantially increased by the further inclusion of one or more hydrophilic components that may exhibit physical association in solution at one or more temperature trigger points and also associate with the one or more hydrophilic polymers modified by the incorporation of one or more hydrophilic side groups.

11 Claims, 3 Drawing Sheets

WELLBORE TREATMENT COMPOSITIONS COMPRISING HYDROPHILICALLY MODIFIED POLYMERS AND NONIONIC SURFACTANTS

CROSS-REFERENCE TO RELATED APPLICATIONS

The present application is a divisional application of U.S. application Ser. No. 12/565,621, filed Sep. 23, 2009 now U.S. Pat. No. 8,076,270, which claims the benefit of U.S. Provisional Application Ser. No. 61/100,467, filed Sep. 26, 2008, and are herein incorporated in their entireties for all purposes.

STATEMENT REGARDING FEDERALLY SPONSORED RESEARCH OR DEVELOPMENT

Not applicable.

BACKGROUND

1. Field of the Invention

This invention generally relates to the field of polymers. More specifically, the invention relates to wellbore treatment compositions using hydrophilically modified polymers.

2. Background of the Invention

Associative thickening or gelation of water soluble polymers has many potential applications in such diverse fields as surface coatings, personal care products, drug delivery systems, and other areas requiring rheology modification or colloid stabilization. In particular, such materials have been used in oil extraction such as in oil-field well treatment, enhanced oil recovery, etc. One problem with current wellbore treatment fluids are the high concentrations of polymer required to achieve the necessary viscosity for oilfield applications.

Water soluble polymers modified with hydrophobic side chains, have been investigated with much higher viscosity than similar concentrations of unmodified polymers. This viscosity increase occurs due to association of the hydrophobic side chains, creating a network structure. Hydrophobic polymer modification is commonly achieved by adding alkyl side chains onto a water soluble base polymer. The hydrophobic side chains may also be fluorinated so as to increase hydrophobicity. The polymer modification is progressed via reaction with, for example, a halide, an acyl halide, an anhydride, an epoxide, an amine, or an isocyanate of the required hydrophobic ligand. The size and number of hydrophobic side chains that may be grafted is limited by the solubility of the modified polymer. Hydrophobic polymer modification results in lower solubility, which manifests itself in increase dissolution time or insolubility. The degree of hydrophobic modification is generally limited so as to ensure solubility. The viscosity of aqueous dispersions of polymers modified with hydrophobic side chains reaches a maximum after complete dissolution of the polymer. The viscosity of these solutions decreases as the temperature of the solution is increased. Natrosol Plus, Grade 430, supplied by Hercules is an example of a commercially available water soluble polymer modified with hydrophobic side chains. Hydrophobic modification can be applied to numerous water soluble polymers, including polyvinyl alcohol (PVA), polyacrylic acid (PAA), polymethacrylic acid (PMA), polyacrylamide (PAM), polyethylene oxide (PEO), polypropylene oxide (PPO), carboxymethyl cellulose (CMC), hydroxyethyl cellulose (HEC), hydroxypropyl cellulose (HPC), guar gum, hydroxypropyl guar gum (HPG), carboxymethylhydroxypropyl guar (CM-HPG), dextran, locust bean gum (LBG), welan gum, xanthan gum, scleroglucan, succinoglycan, polypeptides and the like. Nonionic polymers, or predominantly nonionic polymers, generally have greater compatibility with other species in aqueous solution and have broader applicability.

When combined with suitable surfactants, water soluble polymers modified with hydrophobic side chains can provide solutions with much higher viscosity than similar concentrations of polymers modified with hydrophobic side chains alone. The lower concentration of modified polymer generally results in improved solubility, but solubility still limits the degree of hydrophobic modification of the polymer that can be applied. Many anionic surfactants will interact with polymers modified with hydrophobic side chains, in aqueous solution. As an example, sodium dodecyl sulfate (SDS) is a common surfactant that demonstrates interaction in solution with water soluble polymers modified with hydrophobic side chains. A large range of cationic surfactants also associate in solution with polymers modified with hydrophobic side chains.

Synthetic water soluble copolymers that incorporate hydrophobic alkyl moieties, in conjunction with nonionic surfactants have been described. For example, copolymers of acrylamide and dodecylacrylate, along with one or more nonionic surfactants and a mono-valent inorganic salt have been reported. The performance of these essentially ionic synthetic polymers (the nature of which is not essentially changed after incorporation of hydrophobic alkyl moieties) is strongly influenced by water salinity. When no salt is added, the viscosity generation is poor. The ionic character of the polymer backbone can also increase incompatibility with other water soluble species, such as divalent, trivalent or polyvalent ions. This can result in a reduced efficacy, or ultimately precipitation from solution, of the associative copolymer.

The degree of hydrophobic modification of water soluble polymers can be increased, while retaining solubility, by also adding a hydrophilic modification to the same polymer. Hydrophobic-hydrophilic polymer modification has been achieved by grafting ionic side chains onto a water soluble base polymer, along with hydrophobic side chains. The grafting of sulfoalkyl groups along with alkyl groups has been described. The sulfoalkyl group may be added by reaction of a water soluble polymer containing pendant hydroxyl groups with, for example, 3-chloro-2-hydroxy-propane sulfonate, sodium 3-bromopropane sulfonate or sodium vinylsulfonate and the like. For synthetic polymers, the hydrophobic-hydrophilic polymer can be formed by the copolymerization of suitable monomers, at least one of which provides ionic character for the resulting polymer and at least one of which provides hydrophobic character for the resulting polymer. An example of such a co-polymerization is the reaction of an acrylamide with an alkyl methacrylate, forming a poly(co-acrylamide-alkylmethacrylate). Although ionic polymers, or ionically modified polymers, can increase solubility in water, such ionic character can also increase incompatibility with other water soluble species, such as divalent, trivalent or polyvalent ions. This can result in a reduced efficacy, or ultimately precipitation from solution, of the modified associative polymer.

Viscoelastic surfactants are another class of associative materials that have been taught. The viscoelastic surfactant molecules, when present at a sufficiently high concentration, aggregate into micelles, which may take the form of rods or worm-like micelles, resulting in an associative structure that provides an increase in viscosity. Many surfactants may be used to form viscoelastic solutions, for example, N-erucyl-N, N-bis(2-hydroxyethyl)-N-methyl ammonium chloride is a commercially available viscoelastic surfactant. The ionic strength of the solution of viscoelastic surfactants is selected so as to improve viscosity generation. For low salinity water, this generally requires the addition of one or more monovalent halides or salts of organic anions, with the cation being selected from sodium, potassium or ammonium or the like. Even with an adjusted ionic strength, a high concentration surfactant solution is still required in order to provide a significant increase in viscosity. A surfactant concentration in excess of 5% by weight is not uncommon, and even at this concentration the viscosity of systems at elevated temperature is somewhat limiting. The high surfactant concentration also makes viscoelastic surfactant systems commercially unattractive for many applications. The ionic character of the viscoelastic surfactant can also increase incompatibility with other water soluble species, such as divalent, trivalent or polyvalent ions. This can result in a reduced efficacy of the viscoelastic surfactant system.

The use of a viscoelastic surfactant has been combined with a water soluble polymer modified with hydrophobic side chains. The pendant hydrophobic chains interact with the surfactant micelles creating a viscoelastic gel structure. This association occurs below the typical concentration used for pure visco-elastic surfactant systems, thus providing the potential for more commercially viable applications of viscoelastic surfactants. The solubility of the alkyl modified water soluble polymer limits the size and number of hydrophobic chains that may be incorporated into the polymer. Due to the ionic nature of the surfactant incorporated into the system, incompatibility with other water soluble species, such as divalent, trivalent or polyvalent ions can occur. This can result in a reduced efficacy of the system.

Gelation or associative thickening can also be achieved with water soluble polymers containing hydrophilic groups. The use of visco-elastic surfactants combined with a water soluble polymer that, after dissolution and heating to the lower critical solution temperature (LCST) of the polymer, provides a substantial increase in viscosity. For example, a solution of a block-copolymer of PEO and PPO linked by urethane, urea and allophanate bonding units and the viscoelastic surfactant N-erucyl-N,N-bis(2-hydroxyethyl)-N-methyl ammonium chloride that is heated to a temperature greater than the LCST of the polymer, provides higher viscosity than similar concentrations of the same polymer heated to the same temperature when no surfactant is present. Due to the cationic nature of the surfactant incorporated into the system, incompatibility with other water soluble species, such as divalent, trivalent or polyvalent ions can occur. This can result in a reduced efficacy of the system.

The use of a charged polymer along with a surfactant of an opposing charge can also be used to create association in solution. As an example, when a negatively charged ionic polymer, such as CMC, CMHPG, PAA, PMA or the like is mixed in solution with a positively charged surfactant, such as a tetraalkylammonium halide or the like, at suitable concentrations of the components, association is observed via an increase in viscosity compared to similar concentrations of ionic polymer without the addition of surfactant. Similarly, as a further example, when a positively charged ionic polymer, such as poly(2-(dimethylamino)ethyl methacrylate or N-[3-(dimethylamino)propyl]methacrylamide, or a cellulosic water soluble polymer modified by the addition of a quaternary ammonium group or the like, is mixed in solution with a negatively charged surfactant, such as an sodium dodecyl sulfate, or the like, at suitable concentrations of the components, association is observed via an increase in viscosity compared to similar concentrations of ionic polymer without the addition of surfactant. Although these charged polymer-ionic surfactant systems can provide associative thickening, such ionic character increases the incompatibility of these systems with other water soluble species, such as divalent, trivalent or polyvalent ions. This can result in a greatly reduced efficacy of such systems, and ultimately polymer precipitation from solution.

In addition, present wellbore treatments fluids often require the use of separate "breaking" compounds to reduce viscosity after the wellbore treatment fluid's function has been completed such as in a fracture fluid. A disadvantage of existing wellbore treatment fluids, is the incomplete breaking of the viscous wellbore treatment fluid as the addition of breaking compounds are not able to completely break the chemical crosslinks in the wellbore treatment fluids. Thus, the "broken" wellbore treatment fluid still has a relatively high viscosity even after breaking.

Consequently, there is a need for wellbore treatment compositions with improved efficacy (i.e. lower polymer concentration, more effective breaking, elimination of precipitation, etc.).

BRIEF SUMMARY

The disclosed compositions and methods utilize hydrophilic polymers modified by the incorporation of one or more hydrophilic side groups. The polymers may exhibit physical association in solution, and this physical association may be triggered at a specific temperature, so as to provide a significant increase in viscosity. The viscosity of such systems is substantially increased by the further inclusion of one or more hydrophilic components that exhibit physical association in solution at one or more known temperatures and also exhibit physical association with the one or more hydrophilic polymers modified by the incorporation of one or more hydrophilic side groups.

In an embodiment, a wellbore treatment composition comprises a hydrophilically modified polymer. The hydrophilically modified polymer comprises a hydrophilic polymer backbone having one or more nonionic hydrophilic side chains. In addition, the wellbore treatment composition comprises a nonionic surfactant. The nonionic surfactant exhibits thermally triggered physical association with the hydrophilically modified polymer at a temperature trigger point.

In an embodiment, a method of treating a subterranean formation comprises providing a wellbore treatment composition comprising a hydrophilically modified polymer having one or more hydrophilic side chains and a nonionic surfactant. The nonionic surfactant exhibits thermally triggered physical association with the hydrophilic side chains of the hydrophilically modified polymer at a temperature trigger point. The method further comprises injecting the wellbore treatment composition into a wellbore. In addition, the method comprises allowing the wellbore treatment composition to exceed the temperature trigger point prior to reaching the bottom of the wellbore so as to increase the viscosity of the wellbore treatment composition and treat the subterranean formation. The method also comprises reducing the viscosity of the wellbore treatment composition to remove the composition from the wellbore.

In another embodiment, a method of treating a subterranean formation comprises providing a wellbore treatment composition comprising a hydrophilic polymer with one or more hydrophilic side chains, wherein the hydrophilically modified polymer exhibits thermally triggered physical association at a first temperature trigger point of at least about 25° C., and a nonionic surfactant that exhibits thermally triggered physical association at a second temperature trigger point.

The second temperature trigger point is higher than the first temperature trigger point. The method further comprises injecting the wellbore treatment composition into a wellbore. Additionally, the method comprises allowing the wellbore treatment composition to exceed the second temperature trigger point prior to reaching the bottom of the borehole so as to increase the viscosity of the wellbore treatment composition and treating the subterranean formation.

In an embodiment, a method of making a wellbore treatment composition comprises providing a hydrophilic polysaccharide. The method additionally comprises mixing the hydrophilic polysaccharide with a hydrophilic monomer and reacting the hydrophilic polysaccharide to the monomer to modify the hydrophilic polysaccharide with a plurality of hydrophilic side chains.

In an embodiment, the method of making a wellbore treatment composition comprises providing a hydrophilic polysaccharide. The method also comprises mixing the hydrophilic polysaccharide and a first hydrophilic monomer. In addition, the method comprises reacting the hydrophilic polysaccharide to the first monomer to modify the hydrophilic polysaccharide with a plurality of hydrophilic side chains and form an intermediate. Furthermore, the method comprise terminating the aforementioned reaction and removing any unreacted hydrophilic monomer from the intermediate and reacting a second hydrophilic monomer with the intermediate so as to modify the plurality of hydrophilic side chains and form hydrophilic block copolymeric side chains.

A particular aspect of the disclosed methods and compositions is the careful selection of the one or more hydrophilic polymers modified by the incorporation of one or more hydrophilic side groups and the one or more additional hydrophilic components so as to provide significant physical association and substantial thickening.

Another particular aspect of the disclosed wellbore treatment compositions is the development of high viscosity at a low combined concentration of the one or more hydrophilic polymers modified by the incorporation of one or more hydrophilic side groups and the one or more additional hydrophilic components.

One aspect of the disclosed wellbore treatment compositions is the distinct improvement in solubility and rate of dissolution of the said hydrophilic polymers modified by the incorporation of one or more hydrophilic side groups. The modified polymer dissolves more readily in aqueous solutions compared to the same polymer without modification. The dissolution behavior of hydrophilic polymers modified by the incorporation of one or more hydrophilic side groups is far superior to that of hydrophilic polymers modified by the incorporation of hydrophobic side groups.

Embodiments of the novel compositions allow the expected reduction in viscosity with increasing temperature to be avoided, reduced or reversed. By careful formulation using the methods and compositions disclosed herein, the viscosity developed by increasing physical association in solution may be triggered at multiple temperatures. After heating to a first temperature for the initiation of strong physical association between some of the components of the system, further physical association can be initiated at other pre-determined higher temperatures, substantially avoiding, reducing or reversing the expected thermal induced reduction in viscosity.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection or an indirect or direct chemical bond. Thus, if a first molecule couples to a second molecule, that connection may be through a direct bond, or through an indirect bond via other molecules and bonds.

As used herein, the term "associative thickening" may refer to an increase in viscosity of a composition due primarily to physical association or physical cross-linking, as defined herein, as opposed to chemical cross-linking, as defined herein.

As used herein, the term "chemical cross-linking" may refer to the formation of covalent or ionic bonds between polymer chains, polymer side chains, and/or between additives and polymer chains. Polymer cross-linking is well known in the art and may result from the formation of covalent linkages between polymer chains and/or between additives and polymer chains.

As used herein, the term "physical association" or "physical cross-linking" refers to physical interactions (e.g. hydrogen-bonding, van der Waals interactions, coordination interactions, and salt bridges) and/or entanglements between polymer chains, segments of chains, side branches and/or additives in solution. Such interactions may be reversible or irreversible. In addition, such interactions may be intramolecular and/or intermolecular. It is emphasized that no chemical cross-links, either chemical or ionic, are formed as a result of said physical association.

DETAILED DESCRIPTION OF THE PREFERRED EMBODIMENTS

Figure 1:
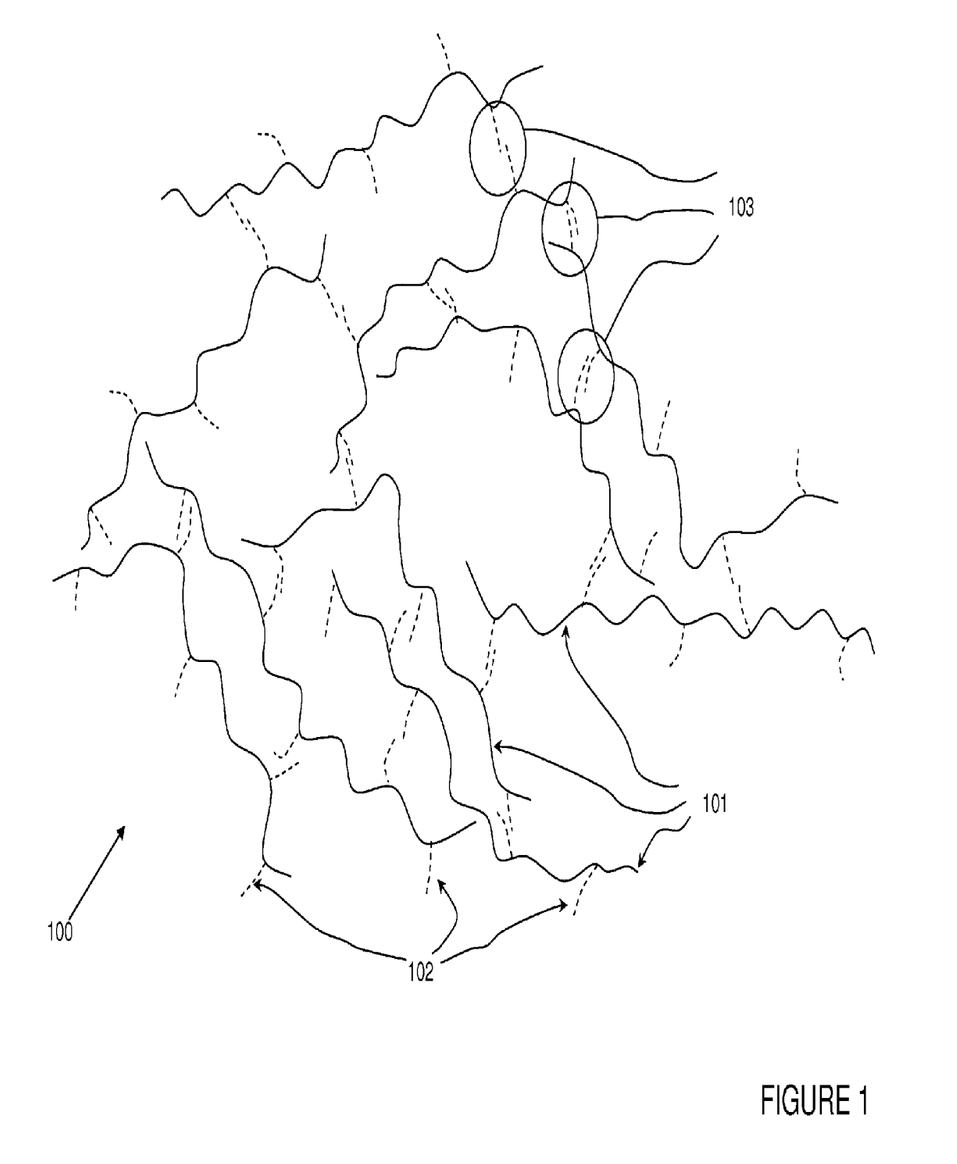
FIG. 1 shows an embodiment of a wellbore treatment composition.

FIG. 1 shows an embodiment of the disclosed wellbore treatment compositions 100 which possess associative thickening properties using hydrophilically modified polymers 101. Without being limited by theory, the disclosed wellbore treatment compositions 100 may exhibit physical association in solution via the interactions 103 of the hydrophilic side chains 102. This physical association can be the result of lower critical solution temperature behavior (LCST)—that is, the disclosed compositions may undergo a micro-phase separation as temperature increases and one or more parts of the composition become less soluble, and self-associate. Furthermore, the wellbore treatment compositions 100 may include one or more additives 106 that exhibit physical association in solution. See FIG. 2.

In some embodiments, the hydrophilically modified polymers 100 may themselves exhibit associative thickening or physical association which may be thermosensitive and/or pH-sensitive. Additionally, the wellbore treatment compositions 100 may also include additives 106 which exhibit thermally triggered or pH triggered physical association with the hydrophilically modified polymers 100. That is, at a temperature trigger point or pH trigger point, the disclosed compositions may exhibit associative thickening (i.e. an increase in viscosity) or may even exhibit gelation. The additives 106 themselves may also exhibit thermally triggered physical association. As used herein, the term "trigger point" may refer to a specific temperature, pH, or some other condition which causes an increase in the viscosity or triggers associative thickening of the wellbore treatment compositions. In some cases, the increase in viscosity may be reversed by a change in temperature, a change in pH, or by the addition of an oxidizing agent or by thermal degradation.

Generally, the polymers to be modified by hydrophilic groups are themselves hydrophilic. The starting polymer may be readily water soluble, but may also have very low water solubility. For example, materials such as cellulose (which has been reported as having very low solubility in pure water) may be modified with hydrophilic groups, resulting in substantially improved water solubility. In particular, as shown in FIG. 1, embodiments of the disclosed compositions comprise a hydrophilic polymer backbone 101 modified with hydrophilic pendant groups or side chains 102 (i.e. branches). The hydrophilic polymer backbone 101 may be one of many suitable polymers known to those of skill in the art. Specifically, the hydrophilic polymer backbones 101 suitable for modification include without limitation, polyvinyl alcohol (PVA), polyacrylic acid (PAA), polymethacrylic acid (PMA), polyacrylamide (PAM), polyethylene oxide (PEO), polypropylene oxide (PPO), a polysaccharide, or combinations thereof. Examples of polysaccharides that may be used as a hydrophilic polymer backbone include without limitation, cellulose, carboxymethyl cellulose (CMC), hydroxyethyl cellulose (HEC), hydroxypropyl cellulose (HPC), guar gum, hydroxypropyl guar gum (HPG), carboxymethylhydroxypropyl guar (CMHPG), dextran, locust bean gum (LBG), welan gum, xanthan gum, scleroglucan, succinoglycan, polypeptide, or combinations thereof. Many commercial hydrophilic polymers, suitable for hydrophilic modification, are readily available, and are suitable for use in embodiments of the composition after hydrophilic modification. Examples include commercially available products such as without limitation, NATROSOL® and GALACTOSOL® supplied by Hercules, CARBOCEL®, POLYFLOS® and VISCOLAM® supplied by Lamberti, RHODOPOL® and RHEOZAN® supplied by Rhodia, BIOZAN®, KELTROL®, and KELZAN® supplied by CP Kelco, or combinations thereof. The hydrophilic polymer backbone 101 may have a molecular weight ranging from about 5,000 to about 5,000,000, alternatively from about 25,000 to about 2,500,000, alternatively from about 200,000 to about 2,000,000.

The polymers 101 modified by the incorporation of one or more hydrophilic side groups 102 and the one or more additional hydrophilic components are nonionic, or predominantly non-ionic, so that the associative thickening is substantially compatible with a wide range of other water soluble additives and contaminants. Alternatively, the polymers 101 modified by the incorporation of one or more hydrophilic side groups and the one or more additional hydrophilic components may also be anionic, cationic or any combination of anionic, cationic and non-ionic.

As disclosed above, the hydrophilic polymer backbone 101 may be modified by one or more hydrophilic side chains 102. Suitable precursors or groups for hydrophilically modifying hydrophilic polymers include nonionic surfactants such as without limitation, alkyl polyalkoxylates, alkyl polyalkoxyglycidylethers, alkylphenol polyalkoxylates, alkylphenyl polyalkoxyglycidylethers, alkyl polyetheramines, polyetheramines, alkylphenyl polyetheramines, polyglycosides, polyglycols, random co-polymer of alkylene oxides, block copolymers of alkylene oxides, or combinations thereof. The block copolymers of alkylene oxides may be diblock, triblock, or multiblock copolymers. One or more of the blocks in these block copolymers may be a random copolymer. In another embodiment, the individual blocks in these block copolymers may be linked by ester linkages or amide linkages so as to allow degradation of the molecule by hydrolysis. In another embodiment, the hydrophilic polymer backbone may be modified by two or more different hydrophilic precursors so as to confer the desired solution properties. At least one of these precursors generally exhibits physical association in solution. The hydrophilic pendant groups may have an alkyl group having from 1 to 30 carbon atoms, alternatively from 1 to 24 carbon atoms, alternatively from 1 to 18 carbon atoms. In some embodiments, the precursors used may be a mixture of products with more than one alkyl chain length. Additionally, the precursors may have molecular weights ranging from about 100 to about 20,000, alternatively ranging from about 200 to about 10,000, alternatively ranging from about 300 to about 6,000.

In one embodiment, the hydrophilic precursor may be a polyetheramine having the following formula:

where $R^1$, $R^2$, and $R^3$ may each be a hydrogen, or an alkyl group. The alkyl group may have any suitable number of carbon atoms. However, in one embodiment, the alkyl group may have from 1 to 5 carbon atoms. $R^1$, $R^2$, and $R^3$ may be the same or different from one another. The subscript "m" is an integer ranging from 1 to 30 and the subscript "n" is an integer ranging from 1 to 30. In an exemplary embodiment, $R^1$ is hydrogen, $R^2$, is a methyl group and $R^3$ is a methyl group and the ratio of m to n equal 1:9. However, the ratio of m to n may be any suitable ratio.

In another embodiment, the hydrophilic precursor may be an alkyl ethoxylate having the following formula:

where $R^1$ be an alkyl group having from 1 to 30 carbon atoms and n ranges from 1 to 30, and $R^2$ may be a hydrogen group or an alkyl group having from 1 to 5 carbon atoms. $R^1$ and $R^2$ may be the same or different from one another. An example of a commercially available alkylethoxylate is NEODOL®, supplied by Shell Chemicals.

The hydrophilic precursor may also be a polyether triblock copolymer having the formula:

or the formula:

where $R^1$ and $R^2$ may each be a hydrogen, or an alkyl group. The alkyl group may have any suitable number of carbon atoms. However, in one embodiment, the alkyl group may have from 1 to 5 carbon atoms. $R^1$ and $R^2$ may be the same or different from one another. The subscripts m, n, and o represent the number of repeating units and may range from 1 to 120. An example of a commercially available series of polyether block copolymers is Pluronic®, supplied by BASF.

It is emphasized that the hydrophilic precursor is not limited to those described above and may be any hydrophilic precursor which imparts specific physical association properties to the hydrophilic polymer backbone 101. The graft density (i.e. the number of hydrophilic branches or side groups per hydrophilic backbone) of the hydrophilic side chain may range from about 0.1 mot % to about 30 mol %, alternatively may range from about 1 mol % to about 20 mol %, alternatively may range from about 2 mol % to about 10 mol %.

It is envisioned that any combination of the disclosed hydrophilic polymer backbones and hydrophilic precursors may be used in the disclosed wellbore treatment compositions. Furthermore, the wellbore treatment compositions may include two or more types of hydrophilically modified polymers.

The hydrophilically modified polymer 100 may be dissolved in a solvent. Typically, the hydrophilically modified polymer 100 may be dissolved in water as an aqueous solution. The aqueous solution may contain other components such as inorganic salts. However, any suitable solvent may be used including without limitation, organic co-solvents miscible with water. Examples of suitable co-solvents include without limitation, alcohols, ketones, glycols, or combinations thereof. As mentioned above, an advantage of the disclosed composition is that the hydrophilically modified polymer need only be present in relatively dilute concentrations. As such, the hydrophilically modified polymer may be in solution at a concentration ranging from about 0.01% w/w to about 2.0% w/w, alternatively from about 0.02% w/w to about 1.5% w/w, and alternatively from about 0.05% w/w to about 1.0% w/w.

Figure 2:
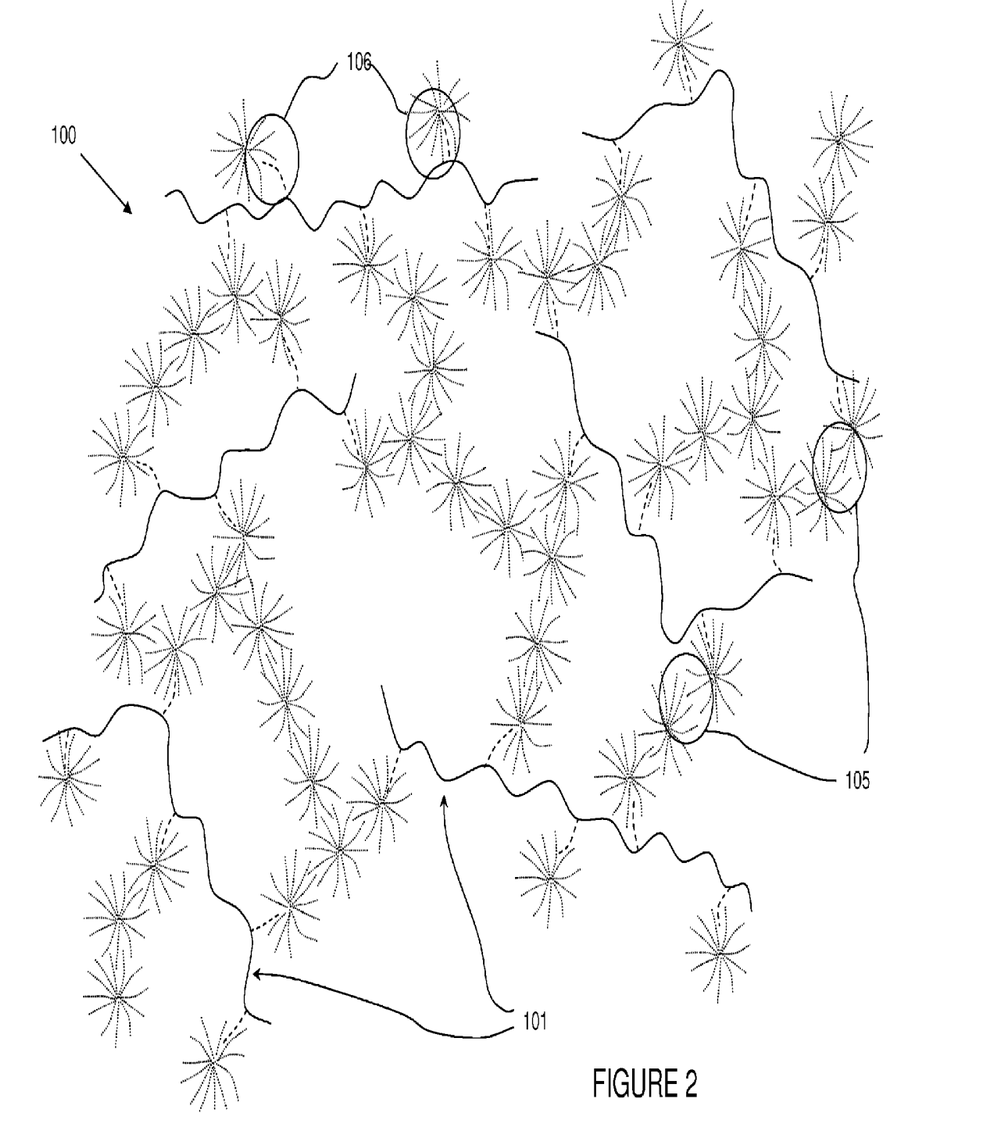
FIG. 2 shows an embodiment of a wellbore treatment composition.

Referring now to FIG. 2, the composition 100 may include an additive 106 to further modulate the physical association of the composition. As used herein, "additive" may refer to a compound which may be added in solution to the hydrophilically modified compound, but does not covalently or ionically bond or react with the hydrophilically modified compound. Instead, the additive 106 may facilitate aggregation or association of the hydrophilically modified compound via physical interactions 105 to cause gelation or thickening. Suitable additives 106 that exhibit physical association in solution include nonionic surfactants, alkyl polyalkoxylates, alkylphenol polyalkoxylates, polyglycols, random co-polymers of alkylene oxides, block copolymers of alkylene oxides, or combinations thereof. Such additives may be exhibit LCST behavior in solution. The block copolymers of alkylene oxides may be diblock, triblock, random, or multiblock copolymers. One or more of the blocks in these block copolymers may be a random copolymer. In another embodiment, the additive may also be degradable. The mechanism for degradation may be hydrolytic degradation. For example, the additive may include a block polymer in which the individual blocks are linked by linkages having the formulas:

where $R^1$ and $R^2$ may each be a hydrogen, or an alkyl group. The alkyl group may have any suitable number of carbon atoms. However, in one embodiment, $R^1$ and $R^2$ may have from 1 to 5 carbon atoms. $R^1$ and $R^2$ may each be the same or different from one another. The subscripts m, m', n, n', and o represent the number of repeating units and may each range from 1 to 120, $X_1$ represents an ester linkage, a diester linkage, an amide linkage, or a diamide linkage, X represents an oxygen atom, an amine group, or an alkyl amine group, and R represents hydrogen or an alkyl group from 1 to 30 carbon atoms in length. Furthermore, $X_1$ may be any functional linkages that may be cleaved by hydrolysis. However, it is contemplated the additive may be degradable by any known mechanisms such as without limitation, thermal degradation, oxidation, etc.

One or more such additives 106 may be used in the formulation of wellbore treatment aqueous based systems described herein. At least one of these said additives 106 exhibits physical association in solution. The additives may contain alkyl groups from 1 to 30 carbon atoms in length, alternatively from 1 to 24 carbon atoms in length, alternatively from 1 to 18 carbon atoms in length. The additives 106 used may be a mixture of products with different alkyl chain lengths. The additives 106 may have a molecular weight ranging from about 100 to about 20,000, alternatively ranging from about 200 to about 10,000, alternatively ranging from about 300 to about 6000.

Many commercial products are readily available that meet the requirements to be suitable additives. Examples include products commercialized under the trademarks PLURONIC® supplied by BASF, NEODOL® supplied by Shell Chemicals, TERGITOL®, TRITON® and ECOSURF® supplied by Dow, SURFONIC® supplied by Huntsman, SYNPERONIC® supplied by Uniqema, and the like.

The additive 106 may be present at any concentration in the wellbore treatment composition. In particular, the additive 106 may be present at concentrations ranging from about 0.01% w/w to about 10.0% w/w, alternatively from about 0.02% w/w to about 5.0% w/w, alternatively from about 0.05% w/w to about 2.0% w/w. Furthermore, the wellbore treatment composition may include two or more different types of additives.

The additives 106 that exhibit physical association in solution may be selected for use based upon their solubility at the planned mixing temperature, their critical micelle temperature, their cloud point in aqueous solution, the total dissolved solids (TDS) of the wellbore treatment compositions, and/or the application temperature of the wellbore treatment compositions. The mixing temperature for application is ranges from about 0° C. to about 75° C., alternatively from about 5° C. to about 60° C., alternatively from about 10° C. to about 50° C. For additives that exhibit a cloud point in solution, the cloud point of a solution of the additives may range from about 5° C. to about 125° C., alternatively from about 15° C. to about 115° C., alternatively from about 25° C. to about 105° C. The TDS of the wellbore treatment compositions may be less than about 100,000 mg/L, alternatively less than about 75,000 mg/L, alternatively less than about 50,000 mg/L. The application temperature of the wellbore treatment compositions ranges from about 15° C. to about 175° C., alternatively ranging from about 25° C. to about 150° C., alternatively ranging from about 35° C. to about 125° C.

The wellbore treatment compositions 100 may possess any suitable temperature trigger points. The temperature trigger point of the wellbore treatment compositions 100 may range from about 0° C. to about 175° C., alternatively ranging from about 25° C. to about 150° C., alternatively ranging from about 35° C. to about 125° C. In addition, as disclosed above, individual components (e.g. hydrophilically modified polymer 101, additives 105) of the wellbore treatment compositions 100 may each have different temperature trigger points. Accordingly, the hydrophilically modified polymer 101 and/or the additives 105 may each have temperature trigger points ranging from about 0° C. to about 175° C., alternatively ranging from about 25° C. to about 150° C., alternatively ranging from about 35° C. to about 125° C.

In an embodiment, at least one of the hydrophilic groups 102 incorporated into the modified hydrophilic polymers does not exhibit strong physical association with other components when the system is heated to the application temperature of the mixed system. This retention of strong hydrophilic behavior by this incorporated hydrophilic group allows more hydrophilic groups that exhibit strong physical associate association to be incorporated into the modified hydrophilic polymers while maintaining solubility of the polymer at elevated temperature.

Hydrophilic modification of the hydrophilic polymer backbone 101 may be performed using any method or reactions known to those of skill in the art. In one embodiment, hydrophilic modification may be achieved by the grafting of a suitable precursor by direct reaction with a suitable pendant group of the hydrophilic polymer, such pendant group being preferably a hydroxyl group, an amino group or a carboxylic acid group. Alternatively, an intermediate of the hydrophilic polymer may be prepared, with which the suitable precursor for hydrophilic modification is generally reacted directly. Alternatively, an intermediate of the suitable precursor for hydrophilic modification may be prepared, which is then reacted directly with the hydrophilic polymer.

The hydrophilic modification may also be achieved by the copolymerization of suitable monomers during the production of the hydrophilic polymer. For example, vinyl alcohol may be copolymerized with a second vinyl compound containing the suitable precursor for hydrophilic modification.

In an embodiment, the hydrophilic modification may also be achieved by a novel in situ polymerization reaction of suitable monomers directly with a hydrophilic polymer. For example, a polysaccharide such as xanthan gum may be reacted with ethylene oxide (EO), propylene oxide (PO), or a mixture thereof, in the presence of a catalyst. Hydroxyl groups on the xanthan gum may be used as the initiation point for the in situ polymerization of the EO, PO or mixed EO/PO monomers. The hydrophilic side chains formed may be homopolymers of EO, PO, and/or random copolymers of EO/PO. The reaction may be terminated by depressurization of the vessel and removal of the un-reacted EO, PO or mixed EO/PO monomers. The reaction conditions and reaction time are selected so as to control the chain length of the EO, PO or EO/PO precursors added to the xanthan polymer. The reaction may be performed in a solvent, or the liquid monomer(s) may be used as the solvent. The preferred solvent is selected based upon the dispersion and dissolution properties of the polysaccharide to be modified.

Cellulose, HEC, HPC, Guar gum, HPG, LBG, PVA, scleroglucan, succinoglycan, welan gum, xanthan gum, or combinations thereof may also be modified by in situ polymerization of the EO, PO or mixed EO/PO monomers and the like. Further, the described reaction of the in situ polymerization of the EO, PO or mixed BO/PO monomers and the like may be applied to any hydrophilic polymer with pendant hydroxyl groups.

Figure 3:
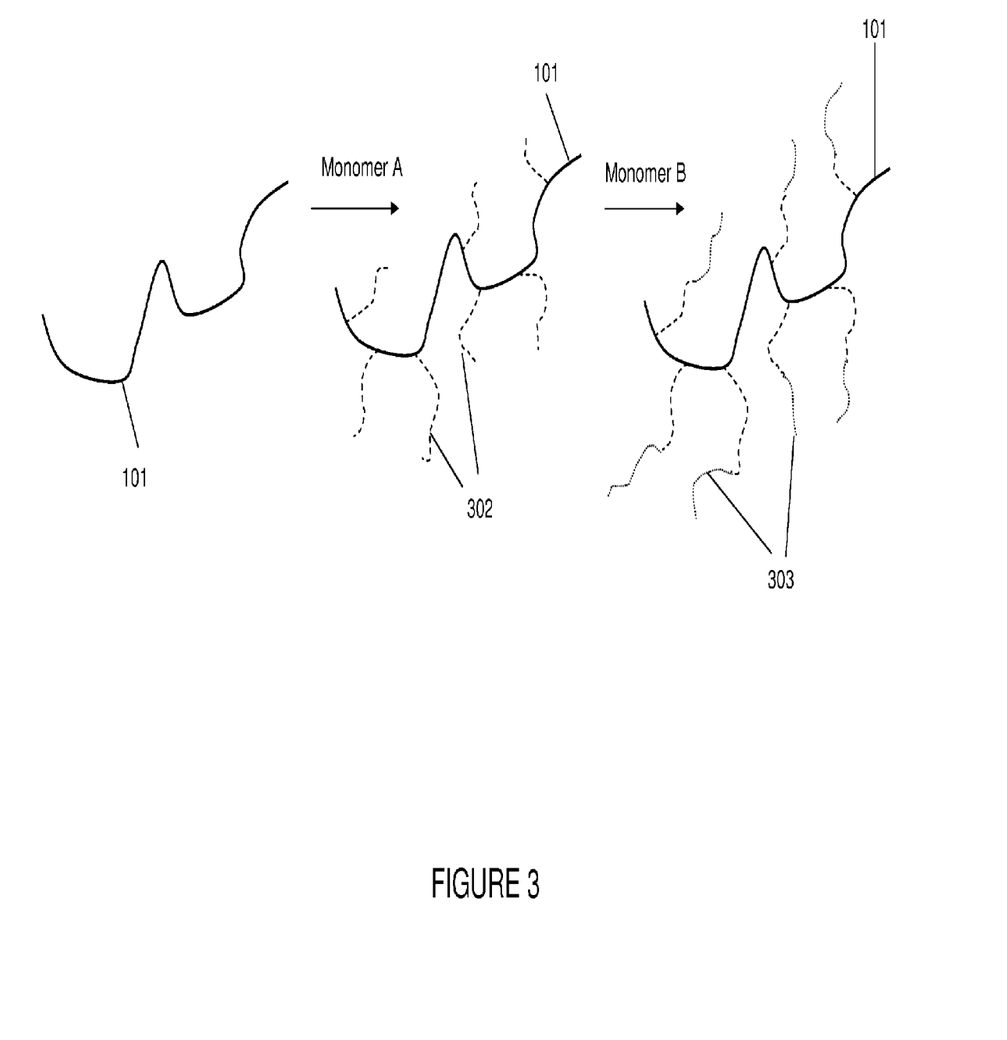
FIG. 3 shows an embodiment of a method of making a wellbore treatment composition.

Alternatively, block copolymer side chains of EO and PO may be formed by first reacting the xanthan gum with a first monomer such as EO and allowing the reaction to proceed as shown in FIG. 3. The intermediate formed is the hydrophilic backbone 101 modified with hydrophilic side chains 302 comprising a first block of the first monomer units. The reaction may then be terminated and unreacted first monomer may be removed. A second monomer such as PO may then be added to the intermediate. The second monomer may react with reactive groups (e.g. hydroxyl groups) at the end of the hydrophilic side chains 302 to form another hydrophilic block 303. By repeatedly terminating the reaction and adding new monomers, multi-block side chains may be formed. Accordingly, embodiments of the hydrophilically modified hydrophilic polymer may be engineered so as to create materials with the desired properties of physical association. The reaction may be performed in a solvent.

Cellulose, HEC, HPC, Guar gum, HPG, LBG, PVA, scleroglucan, succinoglycan, welan gum, xanthan gum, or combinations thereof may also be modified by the sequential reaction with selected alkylene oxides, so as to attach multi-block copolymer side chains. Further the above disclosed methods of hydrophilic modification may generally be applied to any hydrophilic polymers containing pendant hydroxyl groups.

In addition to methods previously described, many other methods may also be used for hydrophilic modification of hydrophilic polymers. Examples of reaction schemes provided herein are only illustrative of the range of other suitable methods that may be used for hydrophilic modification of a broad range of hydrophilic polymers.

Xanthan gum may be modified by reaction with any of the hydrophilic precursors described above (e.g. alkyl polyetheramine, an alkylphenyl-polyetheramine, an amine derivative of a block copolymer of alkylene oxides, a non-ionic surfactant containing an amine group or the like). This reaction may be performed as part of the production process for xanthan gum. For example, the alkyl-polyetheramine may be added directly to the broth resulting from the conventional fermentation of xanthan gum. The reaction is sufficiently complete after 15 minutes at 75° C. As an example, this reaction may be performed using Jeffamine M600 supplied by Huntsman, with the broth of any commercially produced xanthan gum. Other suitable amine derivatives may be prepared from alkyl polyalkoxylates, alkylphenol polyalkoxylates and the like by the conversion of the terminal hydroxyl group to an amine. This method may also be applied using a mixture of alkyl polyetheramines. The quantity of the polyetheramine or one of its derivatives used in the hydrophilic modification of hydrophilic polymers, may be selected so as to confer the desired solution properties. The graft density of the polyetheramine may range from about 0.1 mol % to about 30 mol %, alternatively from about 1 mol % to about 20 mol %, alternatively about to 2 mol % to about 10 mol %.

Scleroglucan, succinoglycan, welan gum CMC, CMHPG and the like may also be modified by reaction with alkyl-polyetheramine and the like. Further, the described reaction of the alkyl-polyetheramine and the like may be applied to any hydrophilic polymer with pendant carboxyl groups.

HEC may be modified by reaction with alkyl-polyalkoxyglycidylethers, alkylphenyl-polyalkoxyglycidylethers and the like. Such glycidyl ether derivatives may be prepared from alkyl-polyalkoxylates, alkylphenol-polyalkoxylates and the like by the conversion of the terminal hydroxyl group to a glycidyl ether group by reaction with, for example, epichlorohydrin. The reaction of alkylglycidylethers with polysaccharides is known, and the same or similar methodology may be used for the reaction of alkyl-polyalkoxyglycidylethers, alkylphenyl-polyalkoxyglycidylethers and the like with polysaccharides. For example, an alkyl-polyalkoxylates, such as NEODOL 23-6.5 supplied by Shell Chemicals, is converted to a glycidyl ether and then reacted with HEC in the presence of an alkali, typically at a temperature of between 40° C. and 100° C. This method can also be applied by using a mixture of alkylglycidylethers and the like. The quantity of alkylglycidylethers and the like used in the hydrophilic modification of hydrophilic polymers may be tailored or optimized to confer the desired solution properties. The graft density of the alkylglycidylethers and its derivatives typically range from about 0.1 mol % to about 30 mol %, alternatively from about 1 mol % to about 20 mol %, alternatively from about 2 mol % to about 10 mol %.

Cellulose, HEC, HPC, Guar gum, HPG, LBG, PVA, scleroglucan, succinoglycan, welan gum, xanthan gum, or combinations thereof may also be modified by reaction with alkylglycidylethers and the like. Further, the described reaction of the alkylglycidylethers and their derivatives may be applied to any hydrophilic polymer with pendant hydroxyl groups.

HEC may also be modified by reaction with an isocyanate capped oligomer of the precursor to be used for hydrophilic modification. For example, a mixture of one or more alkyl-polyalkoxylates, alkylphenol polyalkoxylates or the like is mixed with any common isocyanate, such as methylene bis (phenylisocyanate), MDI, in a molar ratio in the order of 2:1. The components are reacted at around 80° C., under nitrogen for around 1 hour, typically without solvent, so as to form a capped oligomer. Said capped oligomer is reacted with the polymer to be functionalized under relatively dry conditions in a non-protic solvent such as DMSO or methylene chloride. The addition of a catalyst such as a tin catalyst, for example dibutyl tin dilaurate (DBTL), or a base catalyst, such as sodium hydroxide, ensures that the reaction is complete within a few minutes at 60° C. The quantity of alkyl polyalkoxylates and the like used in the hydrophilic modification of hydrophilic polymers may be selected so as to confer the desired solution properties. The graft density of the alkyl polyalkoxylates and the like may range from about 0.1 mol % to about 30 mol %, alternatively from about 1 mol % to about 20 mol %, and alternatively from about 2 mol % to about 10 mol %.

Cellulose, HEC, HPC, Guar gum, HPG, LBG, PVA, scleroglucan, succinoglycan, welan gum, xanthan gum and the like may also be modified by reaction with alkyl-polyalkoxylates and the like. Further, the described reaction of the alkyl polyalkoxylates and the like may be applied to any hydrophilic polymer with pendant hydroxyl groups.

Further options for hydrophilic modification of hydrophilic polymers include, but are not limited to, radical attachment of a suitable graft in the presence of a peroxide. Examples of suitable grafts include, but are not limited to the reaction products of an acryoyl chloride or a maleic anhydride with an alkylpolyalkoxylate, alkylphenolpolyalkoxylate or the like.

A wide variety of formulations using the disclosed methods provide utility for associative thickening of aqueous base systems. Examples of formulations provided herein are illustrative of the applicability of the disclosed methods.

The example formulations provided herein generally describe the first addition of a hydrophilic polymer modified with hydrophilic side groups, followed by a second addition of a further additive that exhibits physical association in solution. The order of addition of these components is generally unimportant, and can proceed in any order including the simultaneous addition of both components.

The example formulations provided herein generally describe the addition of one hydrophilic polymer modified with hydrophilic side groups. Formulations with more than one hydrophilic polymer modified with hydrophilic side groups may also be used. Formulations with more than one further additive that exhibit physical association in solution may also be used. Where a hydrophilic polymer with pendant hydroxyl groups is used in an example, said hydrophilic polymer with pendant hydroxyl groups may be substituted with any other hydrophilic polymer with pendant hydroxyl groups in such formulations. Where a hydrophilic polymer with pendant carboxyl groups is used in an example, said hydrophilic polymer with pendant carboxyl groups may be substituted with any other hydrophilic polymer with pendant carboxyl groups in such formulations. Many other additives may be used so as to provide other desired properties for a variety of applications.

Embodiments of the disclosed wellbore treatment compositions may be particularly suitable for hydraulically fracturing a subterranean formation penetrated by a wellbore. Techniques for hydraulically fracturing a subterranean formation will be known to persons of ordinary skill in the art, and involve pumping the wellbore treatment compositions into the borehole and out into the surrounding formation. The fluid pressure is above the minimum in situ rock stress, thus creating or extending fractures in the formation.

In many cases, hydraulic fracturing consists of pumping a proppant-free viscous fluid, or pad, usually water with some fluid additives to generate high viscosity, into a well faster than the fluid can escape into the formation so that the pressure rises and the rock breaks, creating artificial fractures and/or enlarging existing fractures. Then, proppant particles are added to the fluid to form a slurry that is pumped into the fracture to prevent it from closing when the pumping pressure is released. The proppant suspension and transport ability of the treatment base fluid traditionally depends on the type of viscosifying agent added.

In a fracturing treatment, the wellbore treatment compositions described herein may be used in the pad treatment, the proppant stage, or both. The components of the wellbore treatment compositions may be mixed on the surface. Also, the hydrophilically modified polymer 100 may be pumped down tubing to mix downhole, or vice versa. For example, the nonionic surfactant may be added to the hydrophilically modified polymer while injecting the hydrophilically modified polymer into the wellbore to dissolve and disperse the nonionic surfactant into the hydrophilically modified polymer.

The disclosed methods and compositions may be particularly useful where the temperature trigger point of the wellbore treatment compositions is higher than the preparation temperature of the formulations (e.g. surface temperature at the well). In one embodiment of treating a subterranean formation, adding additives 106 as described above may reduce the viscosity of the hydrophilically modified polymer 101 such that the viscosity of the wellbore treatment compositions may be less than that of hydrophilically modified polymer 101 by itself. Furthermore, the viscosity of the wellbore treatment composition 100 may remain the same until injection into a wellbore. Temperatures in the wellbore generally increase with increasing depth. Upon exceeding the temperature trigger point downhole, which is a higher temperature than the surface temperature, the viscosity of the wellbore treatment composition 100 will associatively thicken and increase in viscosity. In some embodiments, the desired temperature trigger point downhole may the temperature trigger point of the additive 106 or the temperature trigger point of the hydrophilically modified polymer 101. Such behavior is contrary to traditional fracture fluids which exhibit a decrease in viscosity as temperature increases. Moreover, traditionally, additives to fracture fluids are meant to increase viscosity not decrease viscosity. Thus, at surface temperature, existing fracture fluids are quite viscous and less easily handled than embodiments of the disclosed wellbore treatment compositions 100, which preferably exhibit low viscosity at surface temperatures.

One of the advantages of the disclosed wellbore treatment compositions may be the preclusion of the use of a breaker fluid or composition. Due to the primarily physical association of the wellbore treatment composition 100, the associative thickening of these compositions typically may be reversible merely by changing the temperature. For example, the physical association may be thermoreversible. That is, the physical association or increased viscosity may be reversed with a reduction in temperature. More specifically, cooling the wellbore treatment composition 100 will result in a decrease in viscosity in contrast to existing fracture fluids. Alternatively, the physical association may be reversed through thermal degradation of the components of the wellbore treatment compositions. In particular, the side chains of the hydrophilically modified polymer and/or the additive 106 may be thermally degrade to decrease the physical association effects. In other words, an increase in temperature may reverse the associative thickening. However, it is also contemplated that a breaker fluid may be used with embodiments of the disclosed wellbore treatment compositions.

The disclosed compositions may also be useful for personal care products, drug delivery systems, oil-field well treatments and enhanced oil recovery. Enhanced oil recovery methods are well known in the art. The application of the disclosed wellbore treatment compositions in enhanced oil recovery utilizes similar methodologies as with fracturing except the wellbore treatment compositions are injected into the reservoir itself to treat the reservoir. The temperature trigger point of the wellbore treatment compositions may be tailored to the temperature of the reservoir such that the wellbore treatment compositions will remain at low viscosity until injected or permeating into the reservoir. Upon injection into the reservoir and exceeding the temperature trigger point, the wellbore treatment composition will associatively thicken and increase in viscosity to treat the reservoir. Breakers, hydrolysis, degradation, temperature reduction, or other methods, already described above may be used to reduce the viscosity and facilitate removal of the wellbore treatment compositions from the reservoir.

As another example, drug delivery systems may be mixed at a temperature lower than body temperature and be designed so that strong associative thickening occurs at body temperature. As another example, a polymer solution for enhanced oil recovery may be mixed at a temperature below reservoir temperature and be designed so that strong associative thickening occurs before or when reservoir temperature is reached. As another example, a well treatment fluid such as a fracturing fluid, may be mixed at a temperature lower than the temperatures encountered in the well-bore and be designed so that strong associative thickening occurs when the well treatment fluid is heated as it is pumped down the well.

To further illustrate various illustrative embodiments, the following examples are provided.

EXAMPLE 1

Modified polymer 1 (MP1): The reaction apparatus was immersed into a refrigerated bath which was set to 0.5° C. The reactor was charged with isopropyl alcohol, followed by the addition of Natrosol 250 GR hydroxyethyl cellulose (Aqualon Corp.) with stirring. A solution was made by adding sodium hydroxide to de-ionized water. The clear base solution was charged to a pressure-equalized addition funnel, and was added dropwise to the reactor. After base addition, the mixture was stirred in the refrigerated bath. The apparatus was transferred to a hood for further reaction. To the cold reaction mixture, glycidyl ether made from JL-80X surfactant alcohol (Huntsman Petrochemical Corporation) was added dropwise, then the mixture was reacted at a temperature of 70-75° C. The reaction product was recovered from the solvent. The white polymer was washed acetone, then dried in vacuo to yield the modified polymer (MP1).

EXAMPLE 2

Modified polymer 2 (MP2): A 3-necked round-bottom glass reactor flask was fitted with an overhead stirrer, adapters for nitrogen inlet and outlet to a bubbler, a thermocouple, and a pressure-equalized addition funnel. Nitrogen sweep was maintained throughout reaction. The reaction apparatus was immersed into a refrigerated bath which was set to 0.5° C. Nitrogen sweep was begun. The reactor was charged with isopropyl alcohol, followed by the addition Natrosol 250 GR Hydroxyethyl Cellulose (Aqualon Corp.) with stirring. A solution was made by adding sodium hydroxide to de-ionized water. The clear base solution was charged to a pressure-equalized addition funnel, and was added dropwise to the reactor. After base addition, the mixture stirred in the refrigerated bath. After reaction, the apparatus was transferred to a hood for further reaction. To the cold reaction mixture, glycidyl ether made from mPEG 350 surfactant alcohol (Aldrich) was added dropwise, then the mixture was reacted at 75° C. The reaction product was recovered from the solvent. The solid product was washed acetone, then dried in vacuo to yield the modified polymer (MP2).

EXAMPLE 3

Modified polymer 3 (MP3): A 3-necked round-bottom glass reactor flask was fitted with an overhead stirrer, adapters for nitrogen inlet and outlet to a bubbler, a thermocouple, and a pressure-equalized addition funnel. Nitrogen sweep was maintained throughout reaction. The reaction apparatus was immersed into a refrigerated bath. Nitrogen sweep was begun. The reactor was charged with isopropyl alcohol, followed by the addition of Natrosol 250 GR hydroxyethyl cellulose (Aqualon Corp.) with stirring. A solution was made by adding sodium hydroxide to de-ionized water. The clear base solution was charged to a pressure-equalized addition funnel, and was added dropwise at a rate sufficient to keep the reaction solution at a temperature below 2.3° C. After base addition, the mixture stirred in the refrigerated bath. After reaction, the apparatus was transferred to a hood for further reaction. To the cold reaction mixture, glycidyl ether made from mPEG 750 surfactant alcohol (Aldrich) was added dropwise, then the mixture was reacted at a temperature of 75° C. The reaction product was recovered from the solvent. The solid product was washed acetone, then dried in vacuo to yield modified polymer (MP3).

EXAMPLE 4

Modified Polymer 4 (MP4): A 3-necked round-bottom glass reactor flask was with an overhead stirrer, adapters for nitrogen inlet and outlet to a bubbler, a thermocouple, and a pressure-equalized addition funnel. Nitrogen sweep was maintained throughout reaction. The reaction apparatus was immersed into a refrigerated bath which was set to 0.5° C. Nitrogen sweep was begun. De-ionized water was charged to the reactor, followed by the addition of Natrosol 250 GR hydroxyethyl cellulose (Aqualon Corp.) with stirring. A solution was made by adding an aqueous solution of sodium hydroxide to deionized water. The clear base solution was charged to a pressure-equalized addition funnel, and was added drop-wise at a rate sufficient to keep the reaction solution at a temperature below 2.3° C. After base addition, the mixture stirred in the refrigerated bath. After reaction, the apparatus was transferred to a hood for further reaction. To the cold reaction mixture, the glycidyl ether made from Polyglykol B01/20 surfactant alcohol (Clariant Corporation) was added drop-wise, and then the mixture was heated and reacted at 75° C.

EXAMPLE 5

Modified polymer 5 (MP 5): A 3-necked round-bottom glass reactor flask was fitted with a magnetic stirring bar, adapters for nitrogen inlet and outlet to a bubbler, a thermocouple, and a water-cooled condenser. The apparatus was heated then was cooled under nitrogen sweep to remove moisture. The nitrogen sweep was maintained throughout reaction. Anhydrous tetrahydrofuran was added with stirring under nitrogen sweep. Then guar gum (Supercol U Guar from Aqualon Corp.) was charged via powder funnel. To the ensuing slurry, the glycidyl ether made from Neodol 91-8 surfactant alcohol (Shell Chemical LP) was added dropwise. After the addition of ether, a catalyst solution (made by dissolving aluminum (III) trifluoromethyl sulfonate per milliliter in anhydrous tetrahydrofuran) was added via syringe to the reaction mixture. The mixture was heated to 50-60° C., and was held with stirring under nitrogen overnight. After reaction, the mixture was cooled to ambient temperature, then was filtered using a vacuum filtering flask assembly. The solid was washed with acetone. The beige powder was dried in vacuo to constant weight to yield the modified polymer (MP5).

EXAMPLE 6

Modified polymer 6: A multi-necked round-bottom glass reactor flask was fitted with a magnetic stirring bar, adapters for nitrogen inlet and outlet to a bubbler, a thermocouple, a pressure-equalized addition funnel, and a water-cooled condenser. The apparatus was heated then was cooled under nitrogen sweep to remove moisture. Nitrogen sweep was maintained throughout reaction. The apparatus was charged with anhydrous diglyme, with stirring under nitrogen sweep. Then guar gum (Supercol U Guar from Aqualon Corp.) was charged via powder funnel. To the ensuing slurry, the glycidyl ether made from Neodol 91-8 surfactant alcohol (Shell Chemical LP) was added dropwise. After the addition of ether, lanthanum (III) trifluoromethyl sulfonate was added to the reaction mixture. The reaction slurry was heated to 65° C. and reacted at temperature. The mixture was cooled to ambient temperature, then was filtered on a vacuum filtering funnel and was washed with acetone. The solid was slurried in an isopropyl alcohol:water mixture, then was filtered. The white product was washed with acetone, and then dried in vacuo to yield fine modified polymer (MP6) powder.

EXAMPLE 7

Modified polymer 7 (MP7): A multi-necked round-bottom glass reactor flask was fitted with an overhead stirrer, adapters for nitrogen inlet and outlet to a bubbler, a thermocouple, and a pressure-equalized addition funnel. The reaction apparatus was immersed into a refrigerated bath. Nitrogen sweep was begun. The reactor was charged with de-ionized water, followed by the addition of guar gum (Supercol U Guar from Aqualon Corp.) with stirring. A solution was made by adding an aqueous solution of sodium hydroxide to de-ionized water. The clear base solution was charged to a pressure-equalized addition funnel, and was added dropwise at a rate sufficient to keep the reaction solution at a temperature below 2.3° C. After base addition, the mixture stirred in the refrigerated bath. After reaction, the apparatus was transferred to a hood for further reaction. To the cold reaction mixture, the glycidyl ether made from Polyglykol B11/150 surfactant alcohol (Clariant Corporation) was added dropwise, then the mixture was heated to and reacted at 70-75° C. The reaction product was recovered from the solvent. The solid product was washed acetone, then dried in vacuo to yield fine white modified polymer (MP7).

EXAMPLE 8

Modified polymer 8 (MP8): A 3-necked round-bottom glass reactor flask was fitted with an overhead stirrer, adapters for nitrogen inlet and outlet to a bubbler, and a thermocouple. Nitrogen sweep was maintained throughout reaction. To the reactor, de-ionized water was charged and stirring was begun. To the water, hydroxypropyl guar (Galactasol 40H4FDS1; Aqualon Corp.) was charged, and the mixture was stirred at ambient temperature for 15 minutes, in which time a clear solution resulted. A base solution was made by adding potassium hydroxide to de-ionized water until a clear solution resulted. This base solution was added dropwise to the solution in the reactor and stirred. To this solution, the glycidyl ether of Neodol 23-6.5 surfactant alcohol (Shell Chemical LP) was added dropwise, after which the mixture was heated to 60.0° C. When the solution reached temperature, isopropyl alcohol was added, followed by de-ionized water. The mixture was heated overnight. After reaction, the cloudy mixture was precipitated with vigorous agitation into acetone. The precipitated solid was filtered on a vacuum filtering flask assembly, was washed acetone, and then dried in vacuo to yield modified polymer (MP8).

EXAMPLE 9

The viscosity of aqueous solutions of each of the base polymers and each of the modified polymers described in Examples 1-8 were measured using a Brookfield (LV range) DV-II+ Pro viscometer with RTD temperature-controlled small sample adapter and a SC4-18 or SC4-31 spindle. The hydrophilic modifications impacted the viscosity of the base polymers, generally resulting in an increase in viscosity (Table A). As used in Table A, HEC refers to the Natrosol 250 GR hydroxyethyl cellulose, HPG refers to hydroxypropyl guar-Galactasol 40H4FDS1 and Guar refers to Supercol U Guar from Aqualon Corp.

TABLE A

| Sample | Concentration, % w/v | Temperature | Viscosity, cP @ 10 sec$^{-1}$ | Viscosity Vs. Base Polymer |
|---|---|---|---|---|
| HEC | 2.0 | 35 | 99 | — |
| HEC | 2.0 | 70 | 29 | — |
| HPG | 0.5 | 35 | 204 | — |
| Guar | 0.5 | 35 | 274 | — |
| Guar | 0.5 | 70 | 112 | — |
| HP1 | 2.0 | 35 | 40 | 40% |
| MP1 | 0.5 | 35 | 90 | 91% |
| MP2 | 2.0 | 35 | 130 | 131% |
| MP2 | 2.0 | 70 | 39 | 134% |
| MP3 | 2.0 | 35 | 288 | 291% |
| MP3 | 2.0 | 70 | 143 | 493% |
| MP4 | 2.0 | 35 | 114 | 115% |
| MP4 | 2.0 | 70 | 30 | 103% |
| MP5 | 0.5 | 35 | 501 | 183% |
| MP5 | 0.5 | 70 | 209 | 213% |
| MP6 | 0.5 | 35 | 346 | 126% |
| MP6 | 0.5 | 70 | 136 | 121% |
| MP7 | 0.5 | 70 | 122 | 109% |
| MP8 | 0.5 | 35 | 292 | 143% |
| MP8 | 0.5 | 70 | 113 | 113% |

EXAMPLE 10

Comparison of viscosity after addition of different additives are shown in Table B. The viscosity of aqueous solutions of each of the compositions with additives were measured using a Brookfield (LV range) DV-II+ Pro viscometer with RTD temperature-controlled small sample adapter and a SC4-18 or SC4-31 spindle.

TABLE B

| Modified Polymer | Polymer Conc., % w/v | Surfactant | Surfactant Conc., % w/v | Temperature, deg C. | Viscosity, cP @ 10 sec$^{-1}$ | Viscosity Vs. Base Polymer |
|---|---|---|---|---|---|---|
| HP1 | 2.0 | Neodol 23-6.5 | 2.0 | 35 | 137 | 138% |
| MP1 | 2.0 | Neodol 23-6.5 | 2.0 | 35 | 133 | 134% |
| MP2 | 2.0 | Neodol 23-6.5 | 1.0 | 35 | 169 | 201% |
| MP2 | 2.0 | Neodol 23-6.5 | 2.0 | 35 | 199 | 201% |
| MP2 | 2.0 | Neodol 23-6.5 | 1.0 | 70 | 43 | 148% |
| MP2 | 2.0 | Neodol 23-6.5 | 2.0 | 70 | 50 | 172% |
| MP3 | 2.0 | Neodol 23-6.5 | 2.0 | 35 | 359 | 363% |
| MP3 | 2.0 | Neodol 23-6.5 | 2.0 | 70 | 157 | 541% |
| MP4 | 2.0 | Pluronic P123 | 0.1 | 35 | 173 | 175% |
| MP4 | 2.0 | Pluronic P123 | 0.1 | 70 | 41 | 141% |
| MP5 | 0.5 | Neodol 23-6.5 | 2.0 | 70 | 239 | 213% |
| MP6 | 0.5 | Neodol 23-6.5 | 2.0 | 70 | 208 | 186% |
| MP7 | 0.5 | Clariant B11/150 | 6.0 | 70 | 108 | 161% |
| MP7 | 0.5 | Pluronic P123 | 0.1 | 35 | 350 | 128% |
| MP8 | 0.5 | Neodol 23-6.5 | 2.0 | 70 | 127 | 127% |

EXAMPLE 11

The solubilities of the hydrophilically modified polymers were compared to the solubility of a hydrophobically modified polymer (HP1). Hydrophobically Modified Polymer 1 (HP1) was synthesized using the following procedure. A 3-necked round-bottom glass reactor flask was fitted with an overhead stirrer, adapters for nitrogen inlet and outlet to a bubbler, a thermocouple, and a pressure-equalized addition funnel. The nitrogen sweep was maintained throughout reaction. The reaction apparatus was immersed into a refrigerated bath. The reactor was charged with isopropyl alcohol, followed by the addition of Natrosol 250 GR hydroxyethyl cellulose (Aqualon Corp.) with stirring. A solution was made by adding sodium hydroxide to de-ionized water. The clear base solution was charged to a pressure-equalized addition funnel, and was added dropwise to the reactor. After base addition, the mixture stirred in the refrigerated bath. After reaction, the apparatus was transferred to a hood for further reaction. To the cold reaction mixture, the glycidyl ether made from a mixed C12/C14 alkyl alcohol (Erisys® GE-8 surfactant alcohol; Emerald Performance Materials) was added dropwise heated to 75° C. The reaction product was recovered from the solvent. The solid product was washed acetone, then dried in vacuo to yield hydrophobically modified polymer (HP1).

The modified polymers were homogenized in water for 20 minutes and then visually observed. Modified polymers that were not clear solutions after the initial mixing period were continuously stirred until clear solutions were observed. The additional stirring time required to achieve dissolution was reported (Table C). It is evident that the hydrophobically modified polymer (HP1) required a much longer mixing time for full solubility than all of the hydrophilically modified polymers.

TABLE C

| Modified Polymer | Polymer Conc., % w/v | Observation after 20 mins homogenization | Additional stirring time to make clear solution, hours |
|---|---|---|---|
| HP1 | 2.0 | Solid dispersion | 48 |
| MP1 | 2.0 | Hazy | 12 |
| MP2 | 2.0 | Hazy | 12 |
| MP3 | 2.0 | Slightly cloudy | 0.3 |
| MP5 | 0.5 | Clear | — |
| MP6 | 0.5 | Clear | — |

TABLE C-continued

| Modified Polymer | Polymer Conc., % w/v | Observation after 20 mins homogenization | Additional stirring time to make clear solution, hours |
|---|---|---|---|
| MP7 | 0.5 | Clear | — |
| MP8 | 0.5 | Clear | — |

EXAMPLE 12

The viscosity of compositions of a modified polymer and a non-ionic surfactant were measured using a Brookfield (LV range) DV-II+ Pro viscometer with RTD temperature-controlled small sample adapter and a SC4-18 or SC4-31 spindle. At a first lower temperature the viscosity of modified polymer was suppressed, compared to the base polymer, whereas at a second higher temperature, an increase in viscosity compared to the base polymer was observed. (Table D). As used in Table D, HEC refers to the Natrosol 250 GR hydroxyethyl cellulose and Guar refers to Supercol U Guar from Aqualon Corp.

TABLE D

| Polymer | Polymer Conc., % w/v | Surfactant | Surfactant Conc., % w/v | Temperature, deg C. | Viscosity, cP @ 10 sec$^{-1}$ | Viscosity Vs. Base Polymer |
|---|---|---|---|---|---|---|
| HEC | 2.0 | — | — | 20 | 190 | — |
| NEC | 2.0 | — | — | 35 | 99 | — |
| HEC | 2.0 | — | — | 70 | 29 | — |
| MP1 | 2.0 | Neodol 23-6.5 | 2.0 | 20 | 148 | 78% |
| MP1 | 2.0 | Neodol 23-6.5 | 2.0 | 35 | 133 | 134% |
| MP1 | 2.0 | Neodol 23-6.5 | 2.0 | 70 | 34 | 117% |
| Guar | 2.0 | — | — | 20 | 393 | — |
| Guar | 2.0 | — | — | 35 | 274 | — |
| Guar | 2.0 | — | — | 70 | 112 | — |
| MP6 | 0.5 | Neodol 23-6.5 | 2.0 | 20 | 21 | 5% |
| MP6 | 0.5 | Neodol 23-6.5 | 2.0 | 35 | 346 | 126% |
| MP6 | 0.5 | Neodol 23-6.5 | 2.0 | 70 | 136 | 121% |

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

The invention claimed is:

1. A method of treating a subterranean formation comprising:
   a) providing a wellbore treatment composition comprising a hydrophilically modified polymer having one or more hydrophilic side chains and a nonionic surfactant, wherein said nonionic surfactant exhibits thermally triggered physical association with the hydrophilic side chains of the hydrophilically modified polymer at a temperature trigger point;
   b) injecting the wellbore treatment composition into a wellbore;
   c) allowing the wellbore treatment composition to exceed the temperature trigger point prior to reaching the bottom of the wellbore so as to increase the viscosity of the wellbore treatment composition and treat the subterranean formation; and
   d) reducing the viscosity of the wellbore treatment composition to remove the composition from the wellbore.

2. The method of claim 1, wherein (b) comprises adding the nonionic surfactant while injecting the hydrophilically modified polymer into the wellbore to dissolve and disperse the nonionic surfactant into the hydrophilically modified polymer.

3. The method of claim 2 wherein the nonionic surfactant is a solid or a liquid.

4. The method of claim 1 wherein reducing the viscosity of the wellbore treatment composition comprises degrading the wellbore treatment composition by hydrolysis, thermal degradation, oxidation, or combinations thereof.

5. The method of claim 1, further comprising heating the wellbore treatment composition before (b).

6. A method of treating a subterranean formation comprising:
   a) providing a wellbore treatment composition comprising a hydrophilically modified polymer with one or more hydrophilic side chains, wherein the hydrophilically modified polymers exhibits thermally triggered physical association at a first temperature trigger point of at least about 25° C., and a nonionic surfactant that exhibits thermally triggered physical association at a second temperature trigger point, wherein the second temperature trigger point is higher than the first temperature trigger point;
   b) injecting the wellbore treatment composition into a wellbore;
   c) allowing the wellbore treatment composition to exceed the second temperature trigger point prior to reaching the bottom of the borehole so as to increase the viscosity of the wellbore treatment composition; and
   d) treating the subterranean formation.

7. The method of claim 6, further comprising reducing the viscosity of the wellbore treatment composition to remove the composition from the wellbore.

8. The method of claim 6, further comprising adding another wellbore treatment composition having a nonionic surfactant with a temperature trigger point less than the second temperature trigger point and higher than the first temperature trigger point.

9. A method of treating a reservoir comprising:
   a) providing a reservoir treatment composition comprising a hydrophilic polymer with one or more hydrophilic side chains, and a nonionic surfactant, wherein said nonionic surfactant exhibits thermally triggered physical association with the hydrophilic side chains of said hydrophilically modified polymer at a first temperature trigger point;
   b) injecting the reservoir treatment composition into the reservoir;
   c) allowing the reservoir treatment composition to exceed a temperature greater than the first temperature trigger point after it passes into the reservoir so as to increase the viscosity of the reservoir treatment composition.

10. The method of claim 9 wherein the reservoir treatment composition further comprises a proppant, a pH control component, a chemical cross-linking agent, a clay stabilizer, a chelating agent, a chemical buffer, a breaker, or combinations thereof.

11. The method of claim 9 wherein the proppant comprises sand particles, ceramic particles, or synthetic polymer particles.

* * * * *